US006422863B1

(12) United States Patent
Squicciarini

(10) Patent No.: US 6,422,863 B1
(45) Date of Patent: Jul. 23, 2002

(54) ARTICULATOR TO REALIZE GYPSUM MODELS

(76) Inventor: Gaetano Squicciarini, Via Conca d'oro 250, 00161 Rome (IT)

(*) Notice: Subject to any disclaimer, the term of this patent is extended or adjusted under 35 U.S.C. 154(b) by 0 days.

(21) Appl. No.: 09/589,112

(22) Filed: Jun. 8, 2000

(30) Foreign Application Priority Data

Jun. 9, 1999 (IT) ........................................ RM99A0375

(51) Int. Cl.$^7$ ............................................... A61C 11/00
(52) U.S. Cl. ............................................ 433/60; 433/65
(58) Field of Search ................................. 433/54–67

(56) References Cited

U.S. PATENT DOCUMENTS

| 537,812 | A | | 4/1895 | Bragg | |
|---|---|---|---|---|---|
| 3,653,126 | A | * | 4/1972 | Hansen | 433/60 |
| 3,722,099 | A | * | 3/1973 | Jankelson | 433/60 X |
| 3,844,040 | A | | 10/1974 | Willis | |
| 4,164,074 | A | * | 8/1979 | Lawler et al. | 433/65 |
| 4,214,367 | A | * | 7/1980 | Mack | 433/60 |
| 4,337,039 | A | | 6/1982 | Martin et al. | |
| 4,522,591 | A | | 6/1985 | Braun et al. | |
| 4,842,242 | A | | 6/1989 | Huffman | |
| 5,352,117 | A | * | 10/1994 | Silva | 433/60 |
| 5,647,744 | A | | 7/1997 | Squicciarini | |
| 5,658,143 | A | | 8/1997 | Kuperman | |
| 5,947,725 | A | | 9/1999 | Squicciarini | |

FOREIGN PATENT DOCUMENTS

DE 4222699 1/1994

OTHER PUBLICATIONS

Color Brochure entitled, "The Future of Plaster Working in the Dental Technician's Art", by Gaetano Squicciarini, Via Conca d'Ora, 352–00141 Rome, Italy.

* cited by examiner

Primary Examiner—Nicholas D. Lucchesi
(74) Attorney, Agent, or Firm—Smith, Gambrell & Russell, LLP

(57) ABSTRACT

The invention relates to an improved articulator (1) to realize gypsum models comprising a fixed lower arm (2) and an articulated upper arm (3), a respective impression bearing plate (5, 6) being provided on said lower (2) and upper (3) arms, removably coupled with the same, said articulator (1) being characterized in that the coupling between each arm (2, 3) and the respective plate (5, 6) is realized by means (9, 10; 12, 13) allowing the adjustment of the position of the plate (6, 6) with respect to the relevant arm (2, 3).

17 Claims, 6 Drawing Sheets

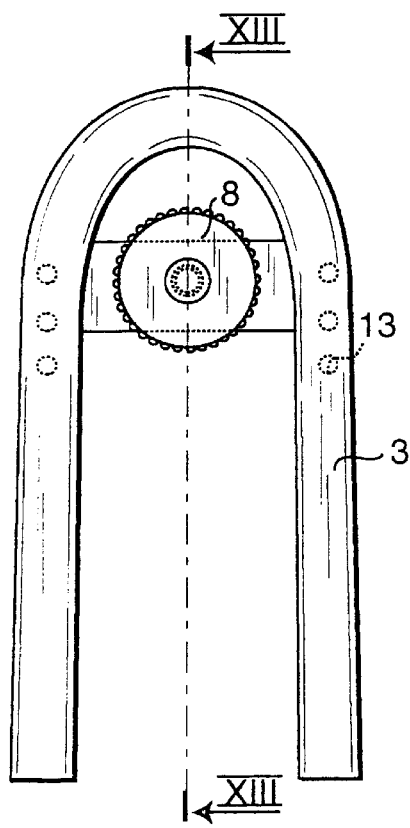
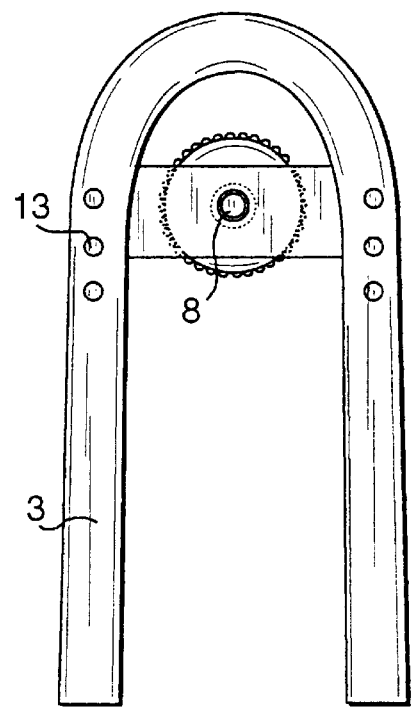
FIG. 11  FIG. 12
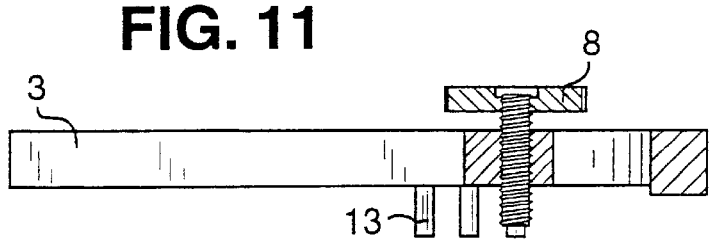
FIG. 13
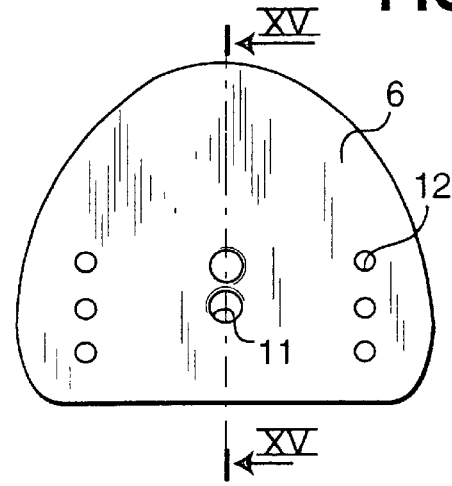
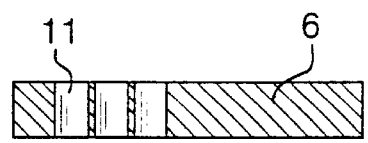
FIG. 14  FIG. 15

ARTICULATOR TO REALIZE GYPSUM MODELS

The present invention relates to an improved articulator to realise gypsum models.

More particulary, the invention relates to an articulator provided with an innovative fixing system of the impression bearing plate, allowing to obtain an optimum positioning of the upper and lower plates, in function of the specific needing of the patient for which the work is being realised.

As it is well known, many articulators are available on the market, all realised with particular technical and structural features.

An impression bearing plate must be positioned on the above and on the bottom on each of the articulators, on which the gypsum model must be cast.

The same Applicant has filed in the past many patent applications concerning element kit allowing to carry out the casting of the gypsum for the realisation of gypsum models.

However, the Applicant has noted that the problem exists of the position each other of the two impression bearing plates on the upper and lower articulator, that cannot be modified in function of the specific needing.

These and other results are obtained according to the invention suggesting an articulator allowing to adjust the position of the plate in function of the specific needing.

It is therefore specific object of the present invention, an improved articulator to realise gypsum models comprising a fixed lower arm and an articulated upper arm, a respective impression bearing plate being provided on said lower and upper arms, removably coupled with the same, said articulator being characterised in that the coupling between each arm and the respective plate is realised by means allowing the adjustment of the position of the plate with respect to the relevant arm.

In a first embodiment of the articulator according to the invention, said means for the adjustment of the position of the plate with respect to the relevant arm are comprised of a plurality of ribs and of a plurality of corresponding grooves, realised on the lower or upper arm and on the respective plate, or vice versa, a plurality of holes being provided on the plate for the removable coupling with the relevant arm.

In a second embodiment of the articulator according to the invention, said means allowing the adjustment of the position of the plate with respect to the relevant arm are comprised of a plurality of pins and of a plurality of corresponding holes, realised on the lower or upper arm and on the relevant plate, or vice versa a plurality of holes being provided on the plate for the removable coupling with the relevant arm.

Preferably, according to the invention, the removable coupling between the plate and the relevant arm is obtained by a threaded pin, In third embodiment of the articulator according to the invention said means allowing the adjustment of the position of the plate with respect to the relevant arm are comprised of continuous means, preferably a central groove realised on said plate upon which a pin coupled to the relevant arm acts.

The present invention will be now described, for illustrative but not limitative purposes, according to its preferred embodiments, with particular reference to the figures of the endosed drawings, wherein:

FIG. 11 shows the arm of FIG. 9 without the plate;

FIG. 12 is a bottom view of the arm of FIG. 11;

FIG. 13 is a section view taken along line XIII—XIII of FIG. 11;

FIG. 14 is a plan view of the plate of the articulator of FIG. 9;

FIG. 15 is a section view taken along line XV—XV of FIG. 14;

Figure 1:
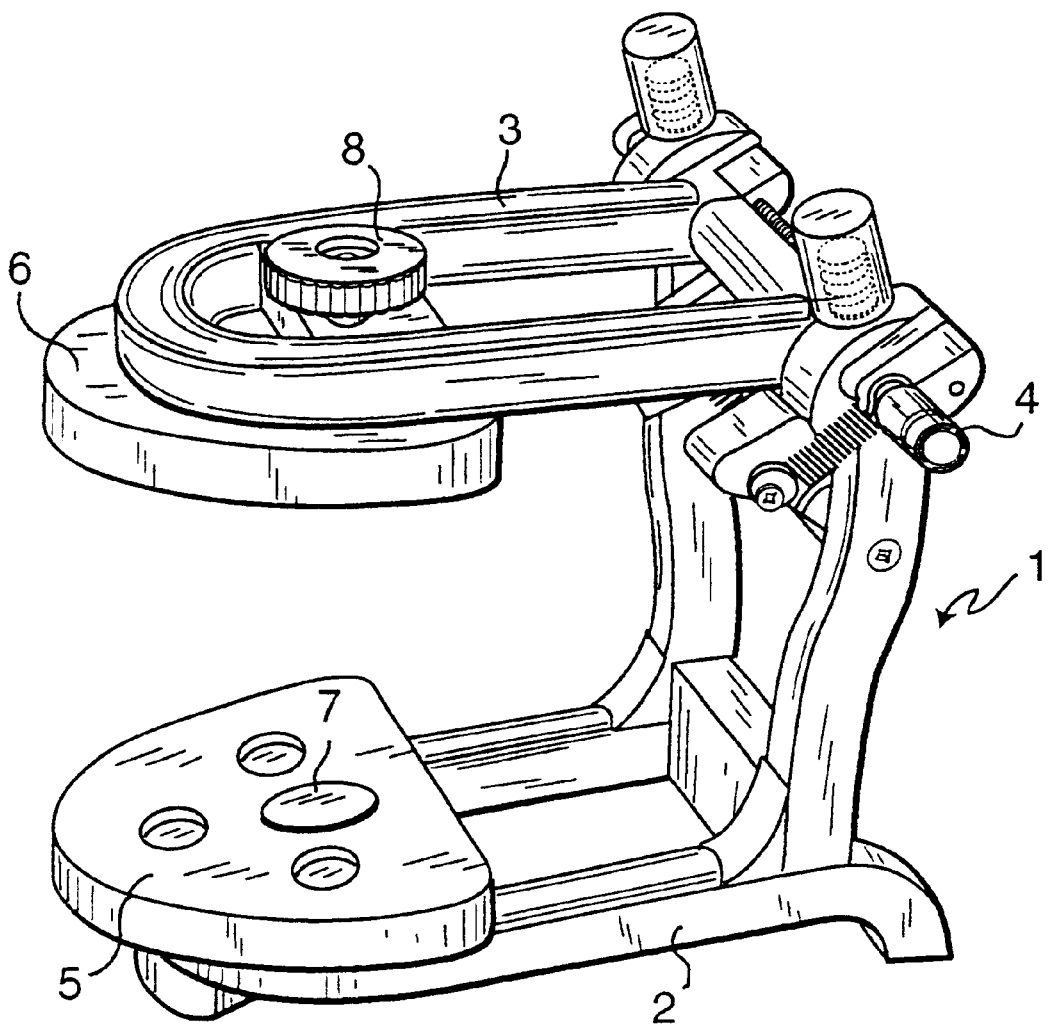
FIG. 1 is a perspective view of a first articulator according to the invention.
Figure 2:
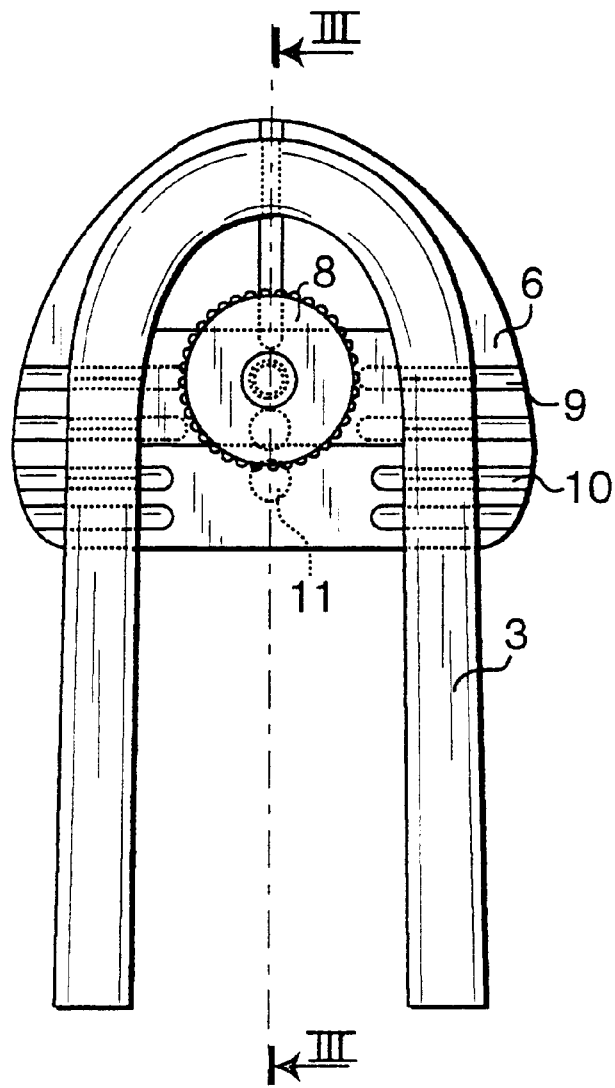
FIG. 2 is a view from the above of an arm with the plate coupled, of a first embodiment of the articulator according to the invention.
Figure 3:
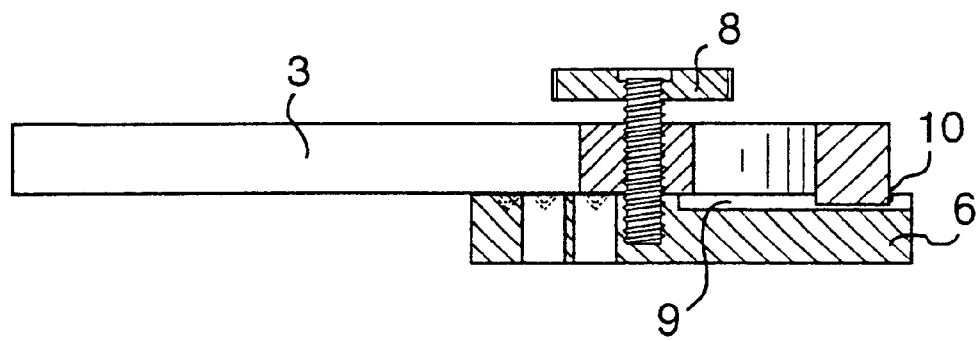
FIG. 3 is a section view taken along the line III—III of FIG. 2.
Figure 4:
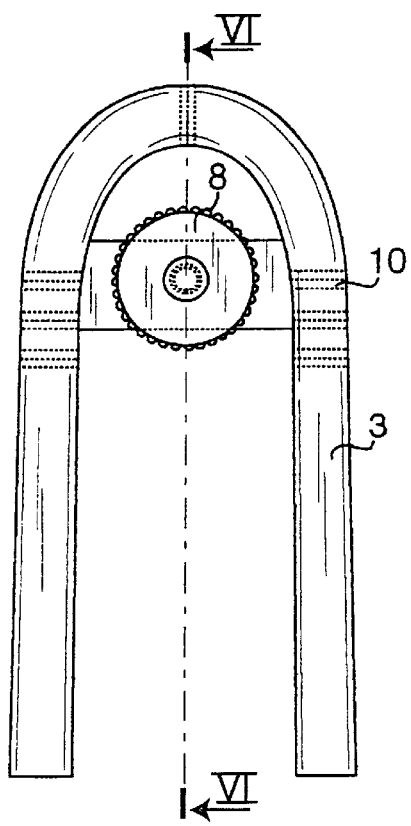
FIG. 4 shows the arm of FIG. 2 without the plate.
Figure 5:
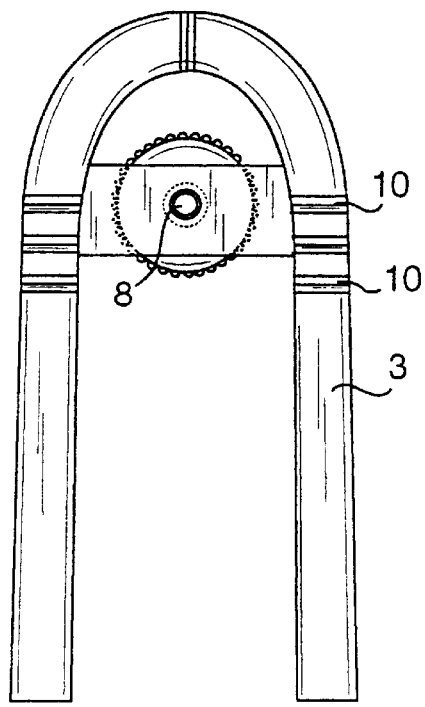
FIG. 5 is a bottom view of the arm of FIG. 4.
Figure 6:
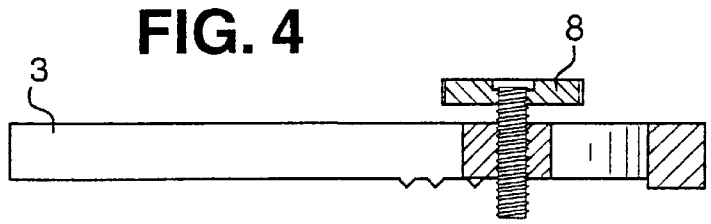
FIG. 6 is a section view taken along line VI—VI of FIG. 4.
Figure 7:
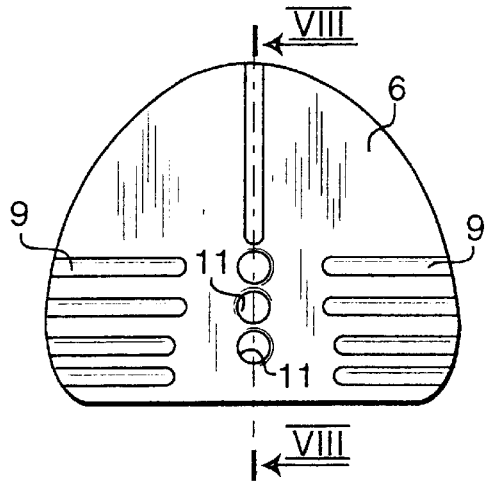
FIG. 7 is a plan view of the plate of the articulator of FIG. 2.
Figure 8:
FIG. 8 is a section view taken along line VIII—VIII of FIG. 7.
Figure 9:
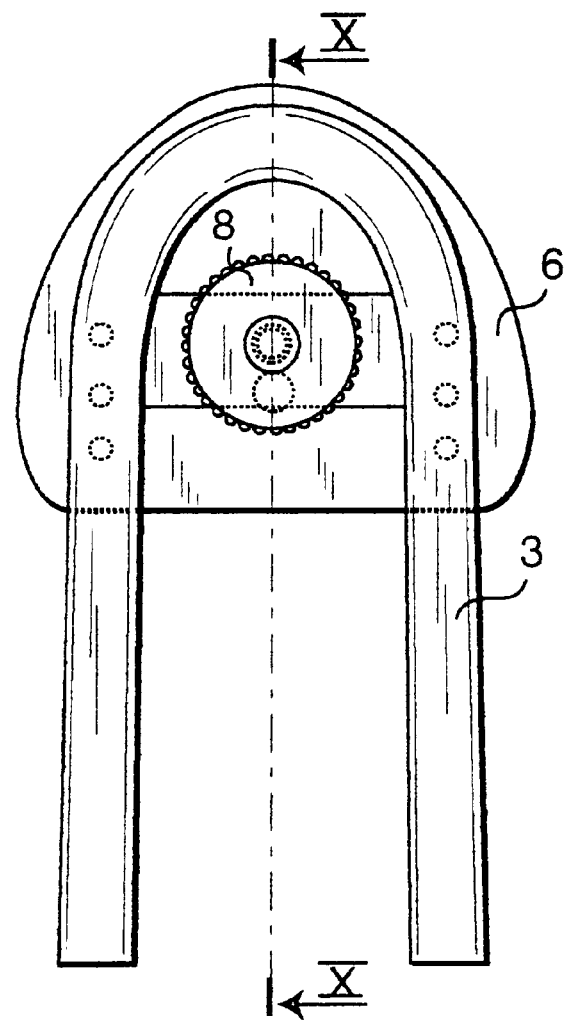
FIG. 9 is a view from the above of an arm with the plate coupled, of a second embodiment of the articulator according to the invention.
Figure 10:
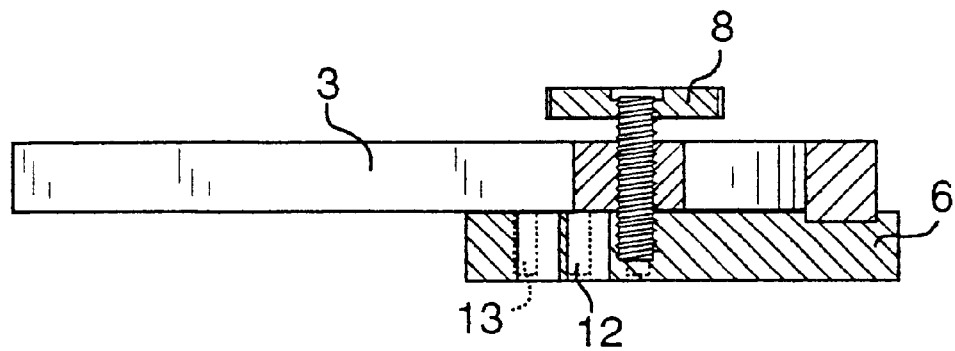
FIG. 10 is a section view taken along the line X—X of FIG. 9.
Figure 19:
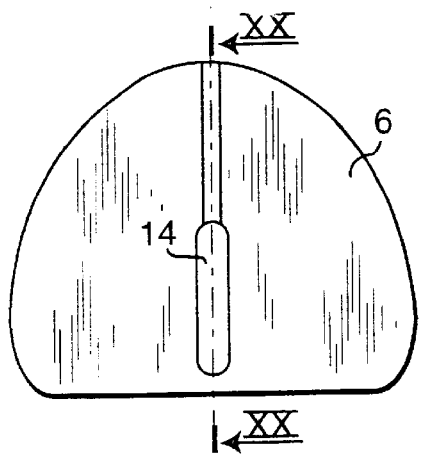
FIG. 19 is a plan view of the plate of the articulator of FIG. 16.
Figure 20:
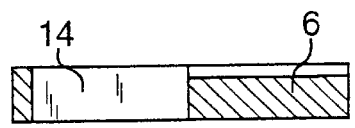
FIG. 20 is a section view taken along line XX—XX of FIG. 19.
Figure 16:
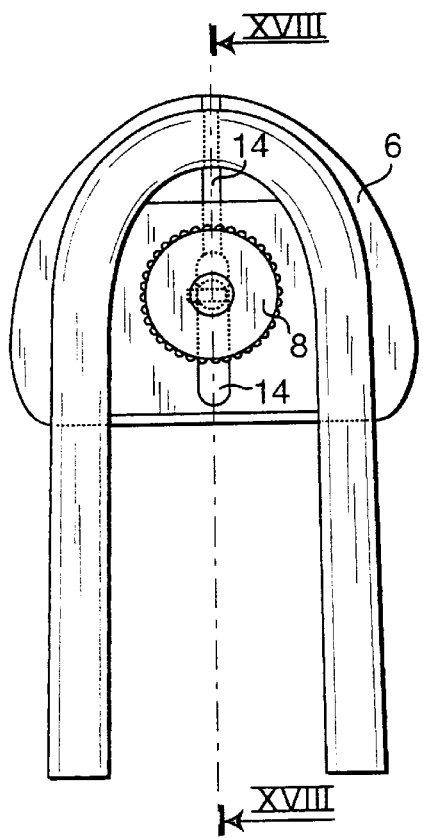
FIG. 16 is a top view of an arm with a coupled plate of a third embodiment of the articulator according to the invention.
Figure 17:
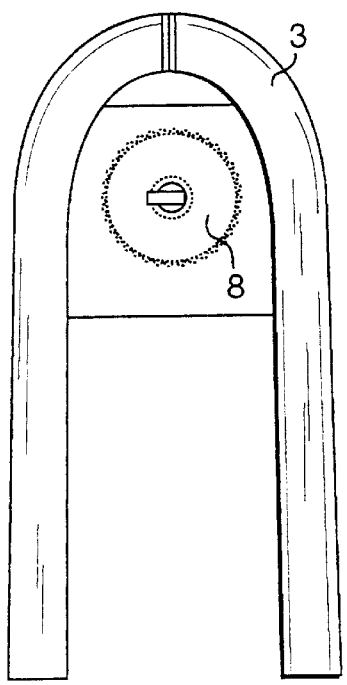
FIG. 17 is a bottom view of the arm of FIG. 16.
Figure 18:
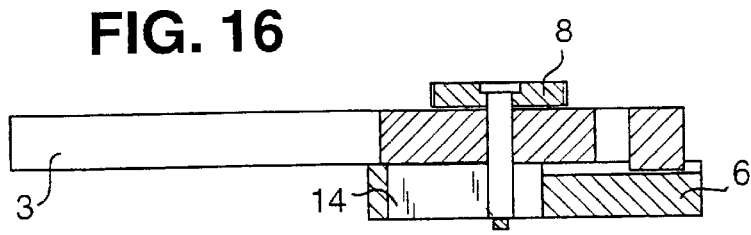
FIG. 18 is a section view taken along line XVIII—XVIII of FIG. 16.

Observing first FIG. 1 of the enclosed drawings, it is shown an articulator 1, that could be also be a different kind of articulator, providing a fixed lower arm, an upper arm 3 articulated in such a way to be possible to lift the same about the axis 4.

Features of the articulator 1 will be not described in greater detail, since it is not part of the invention, and the solution according to the invention could be applied to any other kind of articulator.

Each one of the two arms 2 and 3 provides an impression bearing plate 5, 6, removably coupled to the same by the central threaded pin 7, 8. Obviously, also the fixing of the plate 5, 6 can be realised differently, without departing from the scope of the present invention.

Coming now to observe FIGS. 2–8, it is shown a first embodiment of the present invention. In the figures, and in the relevant specification, it will be made reference to a single arm 2, 3, (in the figures the upper arm 3 is shown), since they are structurally identical.

As it can be noted from the enclosed figures, a plurality of grooves 9 is realised on the plate 6, while corresponding ribs 10 are provided on the arm 3.

In the same way, plate 6 provides a plurality of holes 11 (three in the figures) for the fixing of the pin 8. In this way, it is possible to vary the position of the plate 6 with respect to the arm 3, and thus with respect to the plate 5 of the other arm of the articulator, in such a way to be able to differently adjust the position of the gypsum models in function of the anatomy of the patent for which the work is done.

Coupling of the specific ribs 10 with the corresponding groove 9 allows to obtain different positions. Obviously, the number of grooves 9, of the ribs 10 and of the holes 11 can be different, as well as the positioning of the ribs 10 and of the grooves 9, that could be inverted.

Coming now to observe FIGS. 9–15, it is shown a second embodiment of the present invention. In these figures the same reference numbers will be used to indicate the corresponding parts.

As it can be noted from the enclosed figures, a plurality of holes 12 is realised on the plate 6, while corresponding pins 13 are provided on the arm 3.

In the same way, plate 6 provides a plurality of holes 11 (two in the figures) for the fixing of the pin 8.

In this way, it is possible to vary the position of the plate 6 with respect to the arm 3, and thus with respect to the plate 5 of the other arm of the articulator, in such a way to be able to differently adjust the position of the gypsum models in function of the anatomy of the patient for which the work is done, Coupling of the specific hole 12 with the corresponding pin 13 allows to obtain different positions. Obviously, the number of pins 13, of the holes 12 and of the holes 11 can be different, and they could be inverted.

Observing now FIGS. 16–20, the system to modify the position of the plate 6 on the arm 3 of the articulator can be of the continuous kind, being provided a single fixing system of the pin 8, e.g. along a central rib 14 realised on the plate 6.

The present invention has been described for illustrative but not limitative purposes, according to its preferred embodiments, but it is to be understood that modifications and/or changes can be introduced by those skilled in the art without departing from the relevant scope as defined in the enclosed claims.

What is claimed is:

1. Improved articulator to realise gypsum models comprising a fixed lower arm and an articulated upper arm, a respective impression bearing plate being provided on said lower and upper arms, removably coupled with the same, said articulator being characterised in that the coupling between each arm and the respective plate is realised by means allowing the adjustment of the position of the plate with respect to the relevant arm, and characterised in that said means for the adjustment of the position of the plate with respect to the relevant arm are comprised of a plurality of ribs and of a plurality of corresponding grooves, realised on the lower or upper arm and on the respective plate, or vice versa, and a plurality of holes being provided on the plate with respect to the relevant arm for the removable coupling with the relevant arm.

2. Improved articulator according to claim 1, characterised in that said means allowing the adjustment of the position of the plate with respect to the relevant arm are comprised of a plurality of pins and of a plurality of corresponding holes, realised on the lower or upper arm and on the relevant plate, or vice versa.

3. Improved articulator according to claim 2, characterized in that the removable coupling between the plate and the relevant arm is obtained by a threaded pin.

4. Improved articulator according to claim 2, characterized in that said means allowing the adjustment of the position of the plate with respect to the relevant arm are comprised of continuous means, preferably a central groove realized on said plate upon which a pin coupled to the relevant arm acts.

5. Improved articulator according to claim 1, characterized in that the removable coupling between the plate and the relevant arm is obtained by a threaded pin.

6. Improved articulator according to claim 5, characterized in that said means allowing the adjustment of the position of the plate with respect to the relevant arm are comprised of continuous means, preferably a central groove realized on said plate upon which a pin coupled to the relevant arm acts.

7. Improved articulator according to claim 1, characterized in that said means allowing the adjustment of the position of the plate with respect to the relevant arm are comprised of continuous means, preferably a central groove realized on said plate upon which a pin coupled to the relevant arm acts.

8. An articulator for use in dental model formation, comprising:

a lower arm;

an upper arm, articulable with respect to said lower arm;

an upper impression plate;

a first coupling means for removably coupling said upper impression plate with said upper arm;

a lower impression plate;

a second coupling means for removably coupling said lower impression plate with said lower arm;

said first coupling means including first adjustment means for positional adjustment of the upper impression plate with respect to said upper arm, said first adjustment means including an engageable projection and projection reception combination provided on the upper arm and upper plate for mutual adjustable engagement of the upper impression plate with respect to said upper arm, and said first coupling means including a plurality of holes in said upper impression plate for use in releasably coupling, in different positions, said upper impression plate with said upper arm;

said second coupling means including second adjustment means for positional adjustment of the lower impression plate with respect to said lower arm, said second adjustment means including an engageable projection and projection reception combination provided on the lower arm and lower plate for mutual adjustable engagement of the lower impression plate with respect to said lower arm, and said second coupling means including a plurality of holes in said lower impression plate for use in releasably coupling, in different positions, said lower impression plate with said lower arm.

9. The articulator according to claim 8, wherein the first and second coupling means each comprise a pin dimensioned for insertion into one of said plurality of holes of a respective impression plate.

10. The articulator according to claim 9, wherein each pin is a threaded pin.

11. The articulator according to claim 8, wherein each of said first and second adjustment means comprises a continuous means of adjustment.

12. The articulator according to claim 11, wherein the continuous means of adjustment comprises a central groove provided on each of the first and second impression plates which accepts a projection provided on its respective arm, or vice versa.

13. The articulator according to claim 8, wherein said projection and projection receptor combination includes an engageable rib and groove combination.

14. The articulator according to claim 13, wherein said articulator comprises a plurality of said projection and projection reception combinations.

15. The articulator according to claim 14, wherein said projection and projection reception combinations includes rib and groove combinations.

16. The articulator according to claim 15, wherein a first groove of one of said rib and groove combinations extends in a first direction and a second groove of a second of said rib and groove combinations extends in a second direction perpendicular to said first direction and on a common one of said plates.

17. The articulator according to claim 16, wherein said first groove is a central groove extending in alignment with a direction of spacing of the plurality of holes on the common one of said plates.

* * * * *